(12) United States Patent
Madsen et al.

(10) Patent No.: US 9,212,160 B2
(45) Date of Patent: *Dec. 15, 2015

(54) PHOTOINITIATORS

(71) Applicant: Coloplast A\S, Humlebaek (DK)

(72) Inventors: Niels Joergen Madsen, Alleroed (DK); Petr Sehnal, York (GB); Christian B. Nielsen, Dragoer (DK); David George Anderson, York (GB)

(73) Assignee: Coloplast A/S, Humlebaek (DK)

( * ) Notice: Subject to any disclaimer, the term of this patent is extended or adjusted under 35 U.S.C. 154(b) by 0 days.

This patent is subject to a terminal disclaimer.

(21) Appl. No.: 14/576,237

(22) Filed: Dec. 19, 2014

(65) Prior Publication Data
US 2015/0105565 A1    Apr. 16, 2015

Related U.S. Application Data

(63) Continuation of application No. 13/885,015, filed as application No. PCT/DK2011/050430 on Nov. 11, 2011, now Pat. No. 8,946,449.

(30) Foreign Application Priority Data

Nov. 12, 2010 (DK) ............................. PA 2010 70487
Dec. 22, 2010 (DK) ............................. PA 2010 70572
Jan. 26, 2011 (DK) ............................. PA 2011 70044
Jan. 26, 2011 (DK) ............................. PA 2011 70047

(51) Int. Cl.
| C07D 335/16 | (2006.01) |
|---|---|
| C07D 207/416 | (2006.01) |
| C08F 2/50 | (2006.01) |
| C08G 18/32 | (2006.01) |
| C08G 18/48 | (2006.01) |
| C08G 18/50 | (2006.01) |
| C08G 18/73 | (2006.01) |
| C08G 18/75 | (2006.01) |
| C07C 217/22 | (2006.01) |
| C07C 225/16 | (2006.01) |
| C07C 225/22 | (2006.01) |
| C08J 3/24 | (2006.01) |
| C08J 3/28 | (2006.01) |
| C09D 175/12 | (2006.01) |
| C07C 213/02 | (2006.01) |
| C07C 221/00 | (2006.01) |
| C07C 217/62 | (2006.01) |

(52) U.S. Cl.
CPC ............ *C07D 335/16* (2013.01); *C07C 213/02* (2013.01); *C07C 217/22* (2013.01); *C07C 217/62* (2013.01); *C07C 221/00* (2013.01); *C07C 225/16* (2013.01); *C07C 225/22* (2013.01); *C07D 207/416* (2013.01); *C08F 2/50* (2013.01); *C08G 18/3275* (2013.01); *C08G 18/4833* (2013.01); *C08G 18/5024* (2013.01); *C08G 18/73* (2013.01); *C08G 18/758* (2013.01); *C08J 3/24* (2013.01); *C08J 3/28* (2013.01); *C09D 175/12* (2013.01); *C08J 2375/00* (2013.01)

(58) Field of Classification Search
CPC .................................................... C07D 335/16
USPC ................................................................ 549/27
See application file for complete search history.

(56) References Cited

U.S. PATENT DOCUMENTS

| 4,602,097 A | 7/1986 | Curtis |
|---|---|---|
| 4,861,916 A | 8/1989 | Kohler et al. |
| 4,992,547 A | 2/1991 | Berner et al. |
| 2007/0078246 A1 | 4/2007 | Herr et al. |
| 2010/0049146 A1 | 2/2010 | Nielsen et al. |

FOREIGN PATENT DOCUMENTS

| CN | 1817914 A | 8/2006 |
|---|---|---|
| CN | 101012180 A | 8/2007 |
| CN | 101029095 A | 9/2007 |
| CN | 101495162 A | 7/2009 |
| EP | 0627452 A1 | 12/1994 |
| EP | 1676870 A1 | 7/2006 |
| EP | 2130817 A1 | 12/2009 |
| EP | 2199273 A1 | 6/2010 |
| GB | 2320027 A1 | 6/1998 |
| WO | 9633156 A1 | 10/1996 |
| WO | 9749664 A1 | 12/1997 |
| WO | 9833764 A1 | 8/1998 |
| WO | 9851759 A1 | 11/1998 |
| WO | 03033492 A1 | 4/2003 |
| WO | 2004009651 A1 | 1/2004 |
| WO | 2007092935 A1 | 8/2007 |
| WO | 2008070737 A1 | 6/2008 |
| WO | 2009060235 A1 | 5/2009 |

(Continued)

OTHER PUBLICATIONS

Mukundan et al. "A photocrosslinkable melt processible acrylonitrile terpolymer as carbon fiber precursor." Polymer 47 (2006), pp. 4163-4171.

(Continued)

*Primary Examiner* — Taofiq A Solola

(74) *Attorney, Agent, or Firm* — Coloplast Corp., Coloplast A/S; Nick Baumann

(57) ABSTRACT

The present invention provides novel photoinitiators for polyurethane formation, in which a photoinitiator moiety and a tertiary amine are incorporated into the photoinitiator structure, and thus the polyurethane polymer.

10 Claims, 3 Drawing Sheets

(56) References Cited

FOREIGN PATENT DOCUMENTS

| WO | 2010063612 A1 | 6/2010 |
|---|---|---|
| WO | 2010069758 A1 | 6/2010 |
| WO | 2010072479 A1 | 7/2010 |
| WO | 2011160641 A2 | 12/2011 |
| WO | 2012062333 A1 | 5/2012 |

OTHER PUBLICATIONS

Naskar et al. "UV assisted stabilization routes for carbon fiber precursors produced from melt-processible polyacrylonitrile terpolymer." Carbon 43 (2005), pp. 1065-1072.

Wei et al. "Novel Polymeric, Thio-Containing Photoinitiator Comprising In-Chain Benzophenone and an Amine Coinitiator or Photopolymerization." Journal of Polymer Science: Part A: Polymer Chemistry, vol. 45, pp. 576-587 (2007).

Wei et al: ""Novel PU-type polymeric photoinitiator comprising side-chain benzophenone and coinitiator amine for photopolymerization of PU acrylate"", Polymers for advanced technologies 2008 John Wiley and sons ltd; the Atrium gb, vol. 19, No. 12, 2008, pp. 1763-1770.

J. P. Griffiths et al: ""Surface functional polymers by post-polymerization modification, release and regeneration of hydrogen peroxide and bacterial activity"", LANGMUIR, vol. 26, Jul. 30, 2010, pp. 14142-14153.

J. Wei, H. Wang, X. Jiang, J. Yin, Macromolecules, 40 (2007), 2344-2351.

J. Wei, F. Liu Macromolecules, 42 (2009), 5486-5491.

T. Corrales, F. Catalina, C. Peinado, N.S. Allen J. Polym. Sci., Part A: Polym.Chem., 159 (2003), 103-114.

A. Gilbert, J. Baggott: "Essentials of Molecular Photochemistry", Blackwell, London, 1991.

M.L Gould, S. Narayan-Sarathy, T.E. Hammond, and R.B. Fechter from Ashland Specialty Chemical, USA (2005): "Novel Self-Initiating UV-Curable Resins: Generation Three", Proceedings from RadTech Europe 05, Barcelona, Spain, Oct. 18-20, 2005, vol. 1, p. 245-251, Vincentz.

C.K. Nguyen, W. Kuang, and C.A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz.

J.P. Fouassier: "Excited-State Reactivity in Radical Polymerisation Photo-initiators", Ch. 1, pp. 1-61, in "Radiation curing in Polymer Science and technology", vol. II ("Photo-initiatingSystems"), ed. by J.P. Fouassier and J.F. Rabek, Elsevier, London, 1993.

S. Kopeinig and R. Liska from Vienna University of Technology, Austria (2005): "FurtherCovalently Bonded Photoinitiators", Proceedings from RadTech Europe 05, Barcelona, Spain, 15 Oct. 18-20, 2005, vol. 2, p. 375-381, Vincentz.

J. Med. Chem. 2001, 3810-3820.

J. Med. Chem. 1998, 3976-3986.

J. Med. Chem. 1989, 105-118.

Tetrahedron 2009, 4429-4439.

J. Phys. Org. Chem. 2001, 14, 247-255.

J. Med. Chem. 1991, 34, 1552-1560.

Polymer Synthesis: Theory and Practice, Fundamentals, Methods, Experiments, 4th edition, Springer, 319-324.

Peinado et al: Synthesis of novel 2-(3'-dialkylaminopropoxy)-thioxanthone derivatives. Photochemistry and evaluation as photoinitiators of butyl acrylate polymerization, European Polymer Journal, Pergamon Press Ltd. Oxford, GB, vol. 28, No. 10, Oct. 1, 1992, pp. 1315-1320.

Jianwen yang et al: "Amine-linked Thioxanthones as water-compatible photoinitiators", Journal of polymer science: Part A: Polymer Chemistry, vol. 36, Jan. 1, 1998, pp. 2563-2570.

Gokhan Temel et al: ""Photopolymerization and photophysical properties of amine linked benzophenone photoinitiator for free radical polymerization"", Journal of Photochemistry and photobiology, A: Chemistry, Elsevier Sequoia, Lausanne, CH, vol. 219, No. 1, Jan. 21, 2011, pp. 26-31.

Scott K. Christensen et al: "Gelation of Copolymers with Pendent Benzophenone Photo-Cross-Linkers", Macromolecules, vol. 45, No. 12, Jun. 26, 2012, pp. 5237-5246.

PHOTOINITIATORS

FIELD OF THE INVENTION

The present invention relates to novel photoinitiators. The photoinitiators can be incorporated into polyurethane polymers such that photoinitiator moieties are present as pendant groups on the polymeric backbone.

BACKGROUND OF THE INVENTION

Curing of coatings through ultraviolet (UV) radiation requires efficient methods of initiating the chemical reaction responsible for the curing process. Curing of polymeric material through generation of radical species upon irradiation with UV light is widely used to produce coatings for medical devices. The paint and lacquer industry also makes use of UV-initiated curing of acrylates, where photoinitiators in many cases are employed. These two examples illustrate the diversity of UV curable coatings.

Until recently, polymers designed for use in coatings have relied on photoinitiators with relatively low molecular weight to initiate polymerization (curing). In addition, polymerization reactions often comprise co-reagents and catalysts of the polymerization process which also have relatively low molecular weight. Low molecular weight substances, and their by-products in the polymerization reaction, are generally difficult to remove from the resultant polymer, but instead remain within the polymer matrix and diffuse slowly to the surface of the polymer during its lifetime. Over time, low molecular weight substances therefore leach from the polymer into the surrounding environment.

This presents particular problems in the polymers used in the medical field, as patient safety considerations limit the amount and type of substance which can leach from a given polymer. This is especially relevant if the polymer is to be used as a coating or adhesive which is designed to be in contact with the inside or outside of the patient's body. Notably, certain low molecular weight co-reagents and catalysts of polyurethane polymerization are toxic to plants and animals (e.g. dibutyltin dilaurate (DBTDL) or 1,4-diazabicyclo [2.2.2]octane (DABCO)).

Higher molecular weight photoinitiators, in particular polymeric photoinitiators, have comparably higher intrinsic viscosities which most likely result in longer diffusion times through a matrix. Migration of the UV active substances to the surface is therefore diminished when polymeric photoinitiators are used as opposed to lower molecular weight photoinitiators. Scarce literature within the field of polymeric photoinitiators suggests that development of such polymers could lead to novel applications and present solutions for existing needs, such as providing a material with negligent migration of substances to the surface/patient.

Some descriptions of polymeric photoinitiators are found in scientific literature where, for example, 4-amino-4'-[4-aminothiophenyl]benzophenone is polymerized with toluene-2,4-diisocyanate (J. Wei, H. Wang, J. Yin *J. Polym. Sci., Part A: Polym. Chem.*, 45 (2007), 576-587; J. Wei, H. Wang, X. Jiang, J. Yin, *Macromolecules*, 40 (2007), 2344-2351). Examples of the use of this photoinitiator to polymerize acrylates are also given in this work. A similar strategy is also discussed in J. Wei, F. Liu *Macromolecules*, 42 (2009), 5486-2351, where 4-[(4-maleimido)thiophenyl]benzophenone was synthesized and polymerized into a macromolecular photoinitiator.

A variety of polymeric photoinitiators other than benzophenone based structures are discussed in T. Corrales, F. Catalina, C. Peinado, N. S. Allen *Journal of Photochemistry and Photobiology A: Chemistry*, 159 (2003), 103-114.

US 2007/0078246 describes different aromatic ketone systems which are substituted on a siloxane polymeric chain.

Benzophenone derivatives with pendant alkyl ether substituents have been described in WO 96/33156. Similar structures are described in WO 98/51759 where benzophenone derivatives with pendant alkyl ether groups are presented. A related type of photoinitiator class is described in WO 2009/060235, where thioxanthone moieties are attached to an oligomeric backbone.

Several photoinitiators (e.g. benzophenone, anthraquinone) with pendant polyalkyl ethers are described in WO 97/49664.

WO 03/033492 discloses thioxanthone derivatives attached to a polyhydroxy residue.

U.S. Pat. No. 4,602,097 details water-soluble photoinitiators where two photoinitiator moieties are bridged together by a polyalkylether of sufficient length to make it water soluble.

Many of the prior art references disclose photoinitiators which are end-substituted onto a polymeric entity. However, the photoefficiency of such substances is limited, as they are large molecular weight molecules comprising comparatively little photoinitiator per unit mass.

U.S. Pat. No. 4,861,916 discloses photoinitiators for the photopolymerization of ethylenically unsaturated compounds, in particular in aqueous systems.

EP 2130817 discloses polymerizable Type II photoinitiators. Radiation curable compositions and inks including the multifunctional Type II photoinitiator are also disclosed.

WO2007/092935 discloses hydroxyalkylaminoalkylthioxanthones. CN101012180 discloses mono-component hydrogen extracting photoinitiators.

Despite previous efforts, there remains a need for novel photoinitiators which can reduce by-products of low molecular weight in a polymerization process, particularly polymerization to form polyurethanes. In addition, it would prove useful to reduce or completely remove the need for low molecular weight polymerization catalysts or co-reagents in the polymerization process.

The present invention provides polymer photoinitiators in which the photoinitiator moiety itself becomes an integral part of the polymer, and remains so, during and after the polymerization process. Leaching of photoinitiator and photoinitiator by-products is therefore reduced or even eliminated.

At the same time, the particular design of the photoinitiator allows a reduction in the amount of or even the elimination of co-reagents and catalysts in the polymerization process. In that such substances are minimised or eliminated, their concentrations in the resulting polymers are also reduced, so that leaching of such substances is correspondingly reduced or eliminated. Polymers likely to improve medical safety are thereby obtained.

SUMMARY OF THE INVENTION

The present invention therefore provides a photoinitiator of the general formula (I):

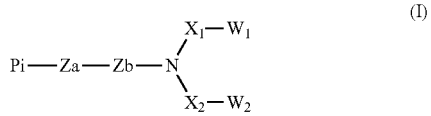

in which:
Pi is a photoinitiator moiety;
Za and Zb together form a single bond, or a linker in which Za is selected from optionally substituted —[O—($C_1$-$C_{12}$ alkylene)]$_n$-, optionally substituted —[NHR$^1$—($C_1$-$C_{12}$ alkylene)]$_n$ wherein R$^1$ is H or optionally substituted $C_1$-$C_{12}$ alkyl and optionally substituted —[S—($C_1$-$C_{12}$ alkylene)]$_n$-, wherein n is an integer from 1-20, wherein Za is joined to Pi via the O, N or S atom in Za, and Zb is a linker moiety;
$X_1$ and $X_2$ are independently selected from optionally substituted $C_1$-$C_{12}$ alkylene, optionally substituted $C_1$-$C_{12}$ alkenylene, optionally substituted heterocyclyl, —O—, —S—, —NR$^2$—, —C(=O)—, —C(=NR$^2$)—, —Si(R$^2$)$_2$—O—, optionally substituted aryl, and combinations thereof, wherein R$^2$ is H or optionally substituted $C_1$-$C_{12}$ alkyl;
wherein $X_1$ and $X_2$ or a part thereof may be linked to one another or to Za or Zb to form one or more ring structures;
wherein Zb, $X_1$ and $X_2$ are selected such that N is a tertiary amine;
$W_1$ and $W_2$ are independently selected from alcohol, primary amine, secondary amine, thiol, alkoxy silane, silyl ester of a carboxylic acid, isocyanate, isothiocyanate, carboxylic acid, chloroformate, primary amide, secondary amide, urethane or urea groups.

The particular structure of the photoinitiator allows it to be incorporated as a monomer into a polyurethane polymer, while initiating polymerization by means of the photoinitiator moiety Pi. In addition, photoinitiators having the general formula (I) are able to at least partially replace nucleophilic low molecular weight amine catalysts (e.g. DABCO) in polyurethane polymerization processes. Furthermore, the use of an alkoxy, amine or thioalkoxy link as Za confers good hydrolytic stability at the same time as providing an improved UV absorption profile due to interaction of the heteroatoms (N, O or S) in Za with the photoinitiator moiety.

The invention also provides a method for the synthesis of a photoinitiator, said method comprising the steps of:
a. reacting a photoinitiator moiety Pi having at least one —OH, —SH or —NHR$^1$ substituent, wherein R$^1$ is H or optionally substituted $C_1$-$C_{12}$ alkyl, in a nucleophilic substitution reaction with a substance having the formula X—($C_1$-$C_{12}$ alkylene)-Y; in which X is a leaving group which can be displaced by said —OH, —SH or —NHR$^1$ substituent, and Y is a leaving group which cannot be displaced by said —OH, —SH or —NHR$^1$ substituent;
b. reacting the product of step a. with sodium iodide in the presence of a base, so as to replace leaving group Y with an iodide; and
c. reacting the product of step ii. with an amine of the formula:

in which $W_1$, $W_2$, $X_1$ and $X_2$ are as defined herein.

Further aspects of the invention are presented in the dependent claims.

FIGURES

DETAILED DISCLOSURE OF THE INVENTION

Definitions

Figure 1A:
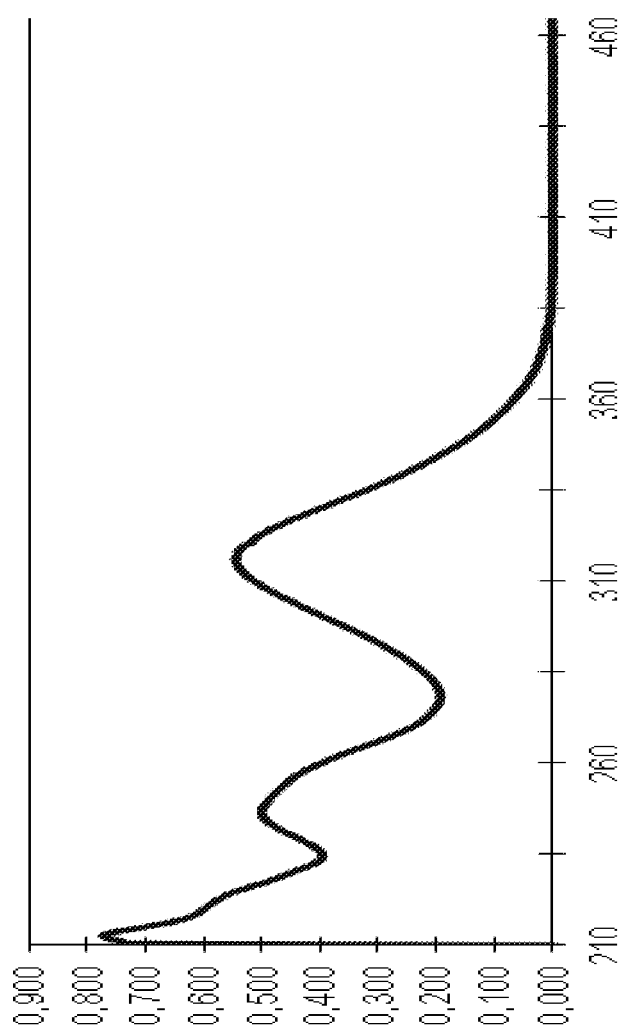
FIG. 1a is shows the UV absorption spectrum of Speedcure BMS (0.001% w/v in methanol, 1 cm path length).

In the following, when a part of a molecule is described as "optionally substituted" it is meant that said part may be substituted by one or more substituents selected from: $C_1$-$C_6$ linear, branched or cyclic alkyl, aryl, —OH, —CN, halogens, amines, amides, alcohols, ethers, thioethers, sulfones and derivatives thereof, sulfoxides and derivatives thereof, carbonates, isocyanates, nitrates and acrylates.

The term "heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom, respectively, is present as a ring atom. The heterocyclyl can be optionally substituted as described above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "alkylene" is used in the following to specify moieties derived from alkanes in which two H atoms have been removed to form a diradical species. The simplest alkylene is methylene —$CH_2$—, and other alkylenes include ethylene —$CH_2$—$CH_2$—, propylene —$C_3H_6$— and butylene —$C_4H_8$—. The term "alkylene" includes branched, linear and cyclic alkylenes, with linear alkylenes being most preferred. An alkylene which is a $C_1$-$C_{12}$ alkylene is one which contains between 1 and 12 carbon atoms. Preferred alkylenes contain between 1 and 6 carbon atoms (i.e. $C_1$-$C_6$ alkylenes).

The term "alkenylene" is used in the following to specify moieties derived from alkenes in which two H atoms have been removed to form a diradical species. Examples include ethenylene —$CH_2$=$CH_2$— and propenylene —$C_3H_4$— moieties. The term "alkenylene" includes branched, linear and cyclic alkenylene, with linear alkenylene being most preferred.

The term "aryl" is used to define an unsaturated cyclic system which contains a delocalised π-electron system about the ring. Aryl groups may comprise from 4-12 atoms, suitably from 6-8 atoms, most suitably 6 atoms. "Aryl" is preferably phenyl (—$C_6H_5$).

The term "aryl" in the present invention is also used to include aromatic heterocycles—rings in which one or more atoms in the ring (e.g. 1-3 atoms) are N, S, P or O. Aromatic heterocycles include pyrrole, furan, thiophene, imidazole, imidazoline, pyrazole, pyrazoline, oxazole, oxazoline, isoxazole, isoxazoline, thiazole, thiazoline, isothiazole, isothiazoline (5-membered rings), pyridine, pyran, thiopyran (6-membered rings).

The term "aryl" also includes fused ring systems.

Polyurethanes

A polyurethane (PU) is a polymer consisting of a chain of organic units joined by urethane (carbamate) links —NH—(C=O)—O—. Polyurethanes are formed by the reaction between one monomer having at least two isocyanate functional groups (—NCO), and another monomer having at least two alcohol (—OH) groups.

The term "polyurethane" when used in accordance with the present invention also includes similar polymers in which the alcohol groups in the monomers are replaced with thiol (—SH) or primary (—NH$_2$) or secondary amine (—NHR) groups. Similarly, the term includes polymers in which the isocyanate groups are replaced with isothiocyanate (—NCS) groups.

Curing

In the present invention, curing is primarily initiated by exposing the photopolymerizable system containing the photoinitiators described in the present invention to high energy irradiation, preferably UV light. The photoinitiated process takes place by methods which are known per se, through irradiation with light or UV irradiation in the wavelength range from 100 to 500 nm. Irradiation sources which may be used are sunlight or artificial lamps or lasers. Mercury highpressure, medium pressure or low-pressure lamps and xenon and tungsten lamps, for example, are advantageous. Similarly, excimer, solid-state and diode-based lasers are advantageous. Diode-based light sources in general are advantageous for initiating the chemical reactions.

The ultraviolet spectrum is divided into A, B and C segments where UV A extend from 400 nm down to 315 nm, UV B from 315 to 280 nm, and UV C from 280 to 100 nm. By using a light source that generates light with wavelengths in the visible region (400 to 800 nm) some advantages are obtained with respect to the depth of the curing, provided that the photoinitiator can successfully cure the material at these wavelength. In particular, scattering phenomena are less pronounced at longer wavelength, thus giving a larger penetration depth in the material. Thus, photoinitiators which absorb, and can induce curing, at longer wavelength are of interest. By judicially choosing substituents on the phenone moieties, the absorption spectrum of the polymeric photoinitiator can to some extent be red-shifted, which would then facilitate curing at comparatively greater depths.

Photoinitiators and Photoinitiator Moieties

The present invention provides photoinitiators suitable for use in the polymerization of polyurethanes having the general formula (I):

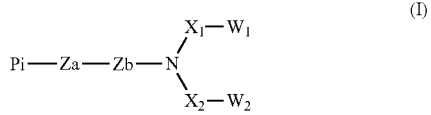
(I)

A photoinitiator is defined as a substance which, on absorption of light, generates reactive species (ions or radicals) and initiates one or several chemical reactions or transformation.

One preferred property of the photoinitiator is good overlap between the UV light source spectrum and the photoinitiator absorption spectrum. Another desired property is a minor or no overlap between the photoinitiator absorption spectrum and the intrinsic combined absorption spectrum of the other components in the polymer matrix. Good compatibility of the photoinitiator in the matrix consisting of material to be cured is also a property of interest.

The photoinitiators with the general formula I comprise a photoinitiator moiety, Pi, which provides the photoinitiators with the required response to UV radiation.

The photoinitiator moieties of the invention are efficient in transforming light from the UV or visible light source to reactive radicals which can abstract hydrogen atoms and other labile atoms from polymers and hence effect polymerization and cross-linking.

Radical photoinitiator moieties can be classified as either cleavable (Norrish type I reaction) or non-cleavable (of which the Norrish type II reaction is a special case, see e.g. A. Gilbert, J. Baggott: "Essentials of Molecular Photochemistry", Blackwell, London, 1991). Upon excitation, cleavable photoinitiator moieties spontaneously break down into two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photoinitiator moieties. Addition of electron donors is not required but may enhance the overall efficiency of cleavable photoinitiator moieties.

Recently, a new class of β-keto ester based photo-initiators has been introduced by M. L Gould, S. Narayan-Sarathy, T. E. Hammond, and R. B. Fechter from Ashland Specialty Chemical, USA (2005): "Novel Self-Initiating UV-Curable Resins: Generation Three", Proceedings from RadTech Europe 05, Barcelona, Spain, Oct. 18-20, 2005, vol. 1, p. 245-251, Vincentz. After base-catalyzed Michael addition of the ester to polyfunctional acrylates, a network is formed with a number of quaternary carbon atoms, each with two neighbouring carbonyl groups. Upon UV or visible light excitation, these photoinitiators predominantly cleave by a Norrish type I mechanism and cross-link further without any conventional photo-initiator present, and thick layers may be cured. Such self-initiating systems are within the scope of the photoinitiator moieties of the present invention.

Excited non-cleavable photoinitiators do not break down to radicals but abstract a hydrogen atom from an organic molecule or, more efficiently, abstract an electron from an electron donor (such as an amine or a thiol). The electron transfer produces a radical anion on the photo-initiator and a radical cation on the electron donor. This is followed by proton transfer from the radical cation to the radical anion to produce two uncharged radicals; of these the radical on the electron donor is sufficiently reactive to abstract a hydrogen atom from most substrates. Benzophenones and related ketones such as thioxanthones, xanthones, anthraquinones, fluorenones, dibenzosuberones, benzils, and phenyl ketocoumarins are important examples of non-cleavable photoinitiators, and fall within the definition of photoinitiator moieties according to the present invention. Most amines with a C—H bond in α-position to the nitrogen atom and many thiols will work as electron donors.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photo-initiators and at the same time spontaneously polymerize by radical addition across the maleimide double bond. In addition, the strong UV absorption of the maleimide disappears in the polymer, i.e. maleimide is a photobleaching photoinitiator moiety; this could make it possible to cure thick layers.

A blend of several photoinitiators may exhibit synergistic properties, as is e.g. described by J. P. Fouassier: "Excited-State Reactivity in Radical Polymerization Photo-initiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photoinitiator moiety to the other in the pairs [4,4'-bis(dimethylamino)benzophenone+benzophenone], [benzophenone+2,4,6-trimethylbenzophenone], [thioxanthone+methylthiophenyl morpholinoalkyl ketone].

However, many other beneficial combinations may be envisaged. So, in an embodiment of the invention, the photoinitiator moiety Pi includes at least two different types of photoinitiator moieties. Preferably, the absorbance peaks of the different photoinitiator moieties are at different wavelengths, so the total amount of light absorbed by the system increases. The different photoinitiator moieties may be all cleavable, all non-cleavable, or a mixture of cleavable and non-cleavable. Preferably, however, the photoinitiator Pi comprises only one photoinitiator moiety.

Furthermore, it has recently been found that covalently linked 2-hydroxy-1-(4-(2-hydroxyethoxy)phenyl)-2-methylpropan-1-one, which is commercially available with the trade name Irgacure 2959, and benzophenone in the molecule 4-(4-benzoylphenoxy ethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalently Bonded Photoinitiators", Proceedings from RadTech Europe 05, Barcelona, Spain, Oct. 18-20, 2005, vol. 2, p. 375-81, Vincentz. This shows that different photoinitiator moieties may show significant synergistic effects when they are present in the same oligomer or polymer. Such covalently linked photoinitiator moieties are also within the scope of the present invention.

Photoinitiator moieties (Pi) in Formula (I) may be selected from, but not exclusively restricted to, the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, camphorquinones, silane and derivatives thereof, and maleimides. Of these, preferred photoinitiator moieties are selected from benzophenones, thioxanthones, benzilketals and phenyl hydroxyalkyl ketones, such as 2-hydroxy-2-methyl-1-phenylpropan-1-ones.

In particular, Pi may be a benzophenone having the general formula (V):

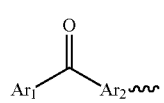

(V)

wherein $Ar_1$ and $Ar_2$ are independently selected from the same or different optionally substituted aryl, and where Za (which binds to $Ar_2$ as shown by the wavy line) may be present at any position on $Ar_2$. Suitably, $Ar_1$ and $Ar_2$ are the same. Benzophenones are well-studied, commercially-available photoinitiator moieties, and their UV absorption can be tailored according to the substitution pattern of the aryl groups. Preferred substituents on $Ar_1$ and $Ar_2$ are electron-donating groups or atoms such as N, O, S, amines, esters or thiols. Such substituents provide UV absorption at a longer wavelength, meaning that LED lamps can be used as a UV source. LED lamps provide advantages such as low energy consumption and generate less heat; thus the substrate temperature can be controlled more accurately. Judicious selection of functional groups can be used to obtain absorption maxima in a desired wavelength region (e.g. impart charge-transfer within the photoinitiator). The ketones described in the present invention are inherent electron accepting groups, so careful selection of electron-donating groups as substituents on aromatic entities within the photoinitiator can lead to absorption profiles matching the light source best suited for the desired curing application. Mechanistically, the efficiency of photoinitiators relies on their ability to intersystem cross from an electronic excited (singlet) state to a triplet state. Some literature has described that such intersystem crossing is less efficient when a higher degree of charge transfer is present within the system. Thus, the absorption profile of a photoinitiator can be controlled to some extent but not without altering the efficiency of radical formation. (see N. J. Turro, *Modern Molecular Photochemistry*, University Science Books: Sausalito, 1991).

In benzophenones of formula (V) above, both $Ar_1$ and $Ar_2$ may be optionally substituted phenyl, preferably both phenyl, and Za may be present at any position on $Ar_2$. Suitably, however, Za is present at the para-position on $Ar_2$, as this provides the maximum opportunity for electron interaction with the carbonyl group, and hence maximum stabilisation of the radical formed.

The particular functionality of Za confers greater hydrolytic stability at the same time as increasing the absorption in the 383-387 nm band region. An example of this effect is the comparison of the UV spectrum of chloro-thioxanthone which has an absorption at 385 nm with a $E_1^{\,1}$ of 159 whereas, its close relative with a propoxy substituent on the aromatic ring, 1-chloro-4-propoxy thioxanthone has an absorption at 387 nm and an $E_1^{\,1}$ of 175. This enhanced extinction coefficient of absorption allows for faster curing.

Figure 1B:
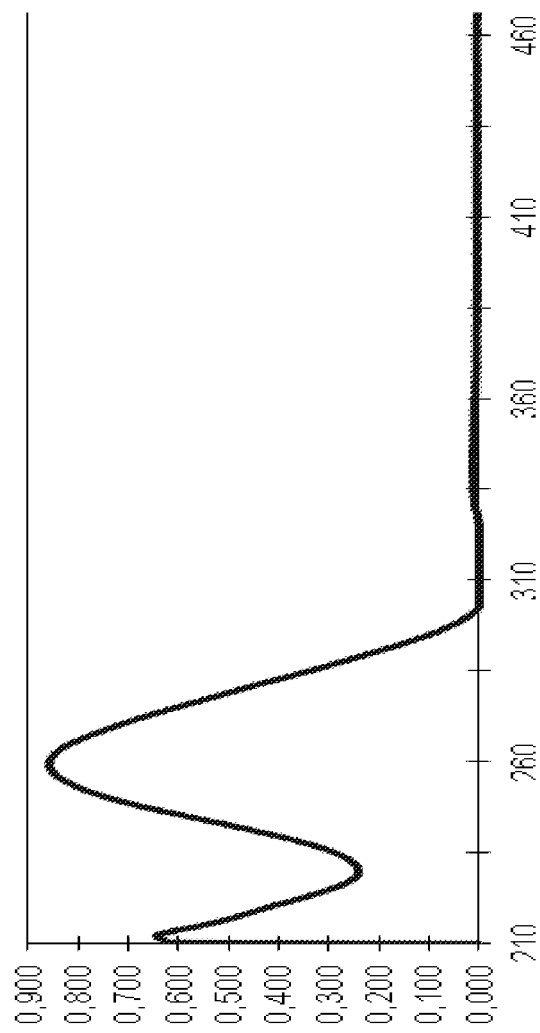
FIG. 1b shows the UV absorption spectrum of Speedcure MBP (0.001% w/v in methanol, 1 cm path length).

A similar effect can be seen in comparing the UV spectra of 4-thiomethyl-benzophenone (BMS) with 4-methyl benzophenone (MBP). The absorption at 316 nm is extremely important in increasing the speed of cure of BMS over MBP. This band is non-existent in MBP. FIGS. 1a and 1b show the UV spectra of BMS and MBP.

Linker, -Za-Zb-

The portion of the photoinitiator of Formula (I) indicated by -Za-Zb- is a linker. The linker -Za-Zb- acts to both bind the photoinitiator moiety to the polyurethane backbone, and simultaneously hold the photoinitiator at a certain distance from the backbone. Linker -Za-Zb- therefore has two ends. At one end, Za is joined to the photoinitiator moiety; at the other end, Zb is joined to the polyurethane backbone.

The size of the linker -Za-Zb- is selected according to the desired properties of the photoinitiator. A short linker -Za-Zb- will provide most opportunity for interaction between the amine group N and the photoinitiator moiety. On the other hand, a long linker -Za-Zb- will provide freer movement of the photoinitiator moiety in the polymerization process, which also provides advantages. A rigid structure may lower the possibility that radicals formed at one site propagate to polymer chains in the vicinity of the photoinitiator, whereas a "loose" structure could facilitate dispersion of radical functionalities over a wider area. Suitably, the linker -Za-Zb- has a molecular weight of less than 10000 Da, suitably less than 5000 Da, most suitably less than 1000 Da. The linker -Za-Zb- preferably comprises no more than 50 atoms, preferably no more than 30 atoms.

In the photoinitiators of Formula (I) above, Zb is a linker moiety. Zb may be selected from a single bond, optionally substituted $C_1$-$C_{12}$ alkylene, optionally substituted $C_1$-$C_{12}$ alkenylene, —O—, —S—, —$NR^1$—, —C(=O)—, —C(=$NR^1$)—, —$SO_2$—, —P(=O)($OR^1$)—, optionally substituted heterocyclyl, optionally substituted aryl, —[O—($C_1$-$C_{12}$ alkylene)]$_n$-, —[$NHR^1$—($C_1$-$C_{12}$ alkylene)]$_n$, —[S—($C_1$-$C_{12}$ alkylene)]$_n$-, and combinations thereof, wherein $R^1$ is H or optionally substituted $C_1$-$C_{12}$ alkyl and n is an integer from 1-20. Most preferably, Zb is a single bond.

Suitably, n is an integer from 1-10, more suitably from 1-5, such as, e.g., 1, 2, 3, 4 or 5.

$R^1$ may be H. $R^1$ may also be optionally substituted $C_1$-$C_6$ alkyl, such as e.g. methyl, ethyl, propyl, butyl, pentyl or hexyl. $R^1$ may be straight-chain, branched or cyclic alkyl.

The invention encompasses photoinitiators in which the linker -Za-Zb- is made up of two or more of the above-mentioned groups in series, e.g.

—O—($C_1$-$C_{12}$ alkylene)-
—O—($C_1$-$C_{12}$ alkylene)-O—($C_1$-$C_{12}$ alkylene)-
—O—($C_1$-$C_{12}$ alkylene)-O-(aryl)-
—$NR^1$—($C_1$-$C_{12}$ alkylene)-
—$NR^1$—($C_1$-$C_{12}$ alkylene)-$NR^1$—($C_1$-$C_{12}$ alkylene)-
—$NR^1$—($C_1$-$C_{12}$ alkylene)-O—($C_1$-$C_{12}$ alkylene)-
—O—($C_1$-$C_{12}$ alkylene)-$NR^1$—($C_1$-$C_{12}$ alkylene)-.

In all of the above, the —($C_1$-$C_{12}$ alkylene)- and -aryl- groups may be substituted or unsubstituted. Other chemically-feasible structures for -Za-Zb- can be determined by the person skilled in the art.

Suitably, Zb is selected from a single bond, optionally substituted $C_1$-$C_{12}$ alkylene, optionally substituted $C_1$-$C_{12}$ alkenylene, —O—, —S—, —$NR^1$—, —[O—($C_1$-$C_{12}$ alkylene)]$_n$-, and combinations thereof, wherein $R^1$ is H or optionally substituted $C_1$-$C_{12}$ alkyl and n is an integer from 1-20. Zb may be selected from a bond, optionally substituted $C_1$-$C_{12}$ alkylene, optionally substituted $C_1$-$C_{12}$ alkenylene, —O—, —S—, —$NR^1$—, and —[O—($C_1$-$C_{12}$ alkylene)]$_n$-, wherein $R^1$ is H or optionally substituted $C_1$-$C_{12}$ alkyl and n is an integer from 1-20. Zb may also be selected from optionally substituted $C_1$-$C_{12}$ alkylene, preferably optionally substituted $C_1$-$C_6$ alkylene. Most preferably, Zb is selected from a bond, optionally substituted $C_1$-$C_6$ alkylene and optionally substituted —O—($C_1$-$C_6$ alkylene)-.

Photoinitiators of Formula (I) in which the linker -Za-Zb- comprises an electron-donating group adjacent Pi are advantageous, as this provides opportunities to tailor the UV absorption of the photoinitiator moiety. Accordingly, Za is selected from optionally substituted —[O—($C_1$-$C_{12}$ alkylene)]$_n$-, optionally substituted —[$NHR^1$—($C_1$-$C_{12}$ alkylene)]$_n$ wherein $R^1$ is H or optionally substituted $C_1$-$C_{12}$ alkyl and optionally substituted —[S—($C_1$-$C_{12}$ alkylene)]$_n$-; wherein n is an integer from 1-20; wherein Za is joined to Pi via the O, N or S atom in Za. Za may also be selected from optionally substituted —O—($C_1$-$C_{12}$ alkylene)-, preferably optionally substituted —O—($C_1$-$C_6$ alkylene)-. This also includes those photoinitiators of Formula (I) in which the linker -Za-Zb- is a bond (i.e. those in which N is directly attached to photoinitiator moiety Pi).

Suitably, in the definition of Za, n is an integer from 1-10, preferably from 1-5, more preferably from 1-3, such as 1, 2 or 3.

$X_1$ and $X_2$

The groups $X_1$ and $X_2$ serve to connect the amine N with the end groups $W_1$ and $W_2$. The size and form of these groups can be varied to adjust the properties of the polyurethane polymer.

$X_1$ and $X_2$ may be the same or different, and are preferably the same, for ease of chemical synthesis. $X_1$ and $X_2$ may be independently selected from optionally substituted $C_1$-$C_{12}$ alkylene, optionally substituted $C_1$-$C_{12}$ alkenylene, —O—, —S—, —C(=O)—, —C(=$NR^2$)—, —Si($R^2$)$_2$—O—, optionally substituted heterocyclyl, optionally substituted aryl, and combinations thereof, wherein $R^2$ is H or optionally substituted $C_1$-$C_{12}$ alkyl. In that $X_1$ and $X_2$ may comprise combinations of the above-mentioned groups, the invention encompasses photoinitiators in which $X_1$ and $X_2$ are made up of two or more of the above-mentioned groups in series.

Suitably, $X_1$ and $X_2$ are independently selected from optionally substituted $C_1$-$C_{12}$ alkylene, optionally substituted $C_1$-$C_{12}$ alkenylene, —O—, —S—, —C(=O)—, —C(=$NR^2$)—, optionally substituted heterocyclyl, optionally substituted aryl, wherein $R^2$ is H or optionally substituted $C_1$-$C_{12}$ alkyl.

$R^2$ may be H. $R^2$ may also be optionally substituted $C_1$-$C_6$ alkyl, such as e.g. methyl, ethyl, propyl, butyl, pentyl or hexyl. $R^2$ may be straight-chain, branched or cyclic alkyl.

$X_1$ and $X_2$ may be linked to one another or to Za or Zb to form one or more ring structures.

$X_1$ and $X_2$ may independently be selected from optionally substituted $C_1$-$C_{12}$ alkylene, —O—, —S—, wherein $R^2$ is H or optionally substituted $C_1$-$C_{12}$ alkyl, and combinations thereof. $X_1$ and $X_2$ may be linked to one another to form one or more ring structures. Additionally, $X_1$ and $X_2$ may independently be selected from optionally substituted $C_1$-$C_{12}$ alkylene, preferably optionally substituted $C_1$-$C_6$ alkylene.

Tertiary Amine, N

In the photoinitiators described by Formula (I), N represents a tertiary amine (i.e. a nitrogen atom bound directly to three carbon atoms, in which the carbon atoms are saturated alkyl or aryl carbon atoms).

The N atom in the photoinitiators in Formula (I) has a number of functions. Firstly, it provides the appropriate branching of the molecule, so that the photoinitiator moieties are pendant from the polyurethane backbone.

Secondly, and more importantly, the N atom in the photoinitiators of Formula (I)—being a tertiary amine—is basic. Suitably, the N atom has a $pK_b$ of less than 13, preferably a $pK_b$ less than 6. The amine N atom is therefore able to partially or completely replace the amine catalysts which are typically used in polyurethane polymerization reactions (e.g. 1,4-diazabicyclo[2.2.2]octane (DABCO), dimethylcyclohexylamine (DMCHA) and dimethylethanolamine (DMEA)). In this way, the use of such low molecular weight tertiary amine catalysts can be reduced or completely avoided.

Thirdly, the tertiary amine in the structure, when irradiated with UV, can have a proton abstracted by the photoinitiator moiety (either intramolecularly or intermolecularly) from the carbon atoms adjacent to the amino nitrogen. This will give rise to an active radical capable of initiating polymerization or cross-linking.

Za, $X_1$ and $X_2$ are selected such that N is a tertiary amine (i.e. so that the atom adjacent N is a saturated carbon atom, or an aryl carbon atom) so that the basic properties of N are preserved. Preferably, at least two of the groups Z, $X_1$ and $X_2$ in the tertiary amine are alkyl.

End groups, $W_1$, $W_2$

The end groups $W_1$ and $W_2$ in Formula (I) allow the photoinitiator to be incorporated into a growing polyurethane chain. $W_1$ and $W_2$ are therefore selected from those functional groups which are reactive in polyurethane monomers, and which are able to bond to other polyurethane monomers to thus form polyurethane. As such, $W_1$ and $W_2$ are independently selected from alcohol, primary amine, secondary amine, thiol, alkoxy silane, silane esters of carboxylic acids, isocyanate, isothiocyanate, carboxylic acid, chloroformate, primary amide, secondary amide, urethane or urea groups. Suitably, $W_1$ and $W_2$ are independently selected from alcohol, primary amine, secondary amine, thiol, tertiary silane, isocyanate, isothiocyanate or carboxylic acid groups.

Secondary amines may have the formula $-NHR^3$, where $R^3$ is optionally substituted $C_1$-$C_{12}$ alkyl. Tertiary silanes may have the formula $-SiH(R^4)_2$, where each $R^4$ independently is optionally substituted $C_1$-$C_{12}$ alkyl.

Suitably, $W_1$ and $W_2$ are independently selected from alcohol, primary amine, secondary amine, or thiol groups.

Care should be taken when selecting suitable $X_1$ and $X_2$ groups, such that $W_1$ and $W_2$ fulfil these criteria. For example, $X_1$ and $X_2$ may independently be selected from optionally substituted $C_1$-$C_{12}$ alkylene, when $W_1$ and $W_2$ are —OH.

$R^3$ and $R^4$ may independently be optionally substituted $C_1$-$C_6$ alkyl, such as e.g. methyl, ethyl, propyl, butyl, pentyl or hexyl. $R^3$ and $R^4$ may be straight-chain, branched or cyclic alkyl.

$W_1$ and $W_2$ are selected according to the design of the polyurethane. If desired, $W_1$ and $W_2$ may be different end groups. It is preferably for ease of synthesis of the photoinitiator, however, that $W_1$ and $W_2$ are the same.

In that only two end groups $W_1$ and $W_2$ are present, the photoinitiator does not promote branching of the polyurethane. Instead, the photoinitiators of Formula (I) are incorporated partly into the polymer chain, while the photoinitiator moieties are pendant from the chain via linker -Za-Zb-.

Further Photoinitiator Structures

A sub-structure which describes photoinitiators of Formula I has the general formula (Ia)

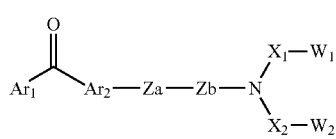

(Ia)

wherein $Ar_1$, $Ar_2$, Za, Zb, N, $X_1$, $X_2$, $W_1$ and $W_2$ are as defined above and where Za may be present at any position on $Ar_2$. In the photoinitiators of Formula Ia, $Ar_1$ and $Ar_2$ may both be optionally substituted phenyl, and are preferably both phenyl. Suitably, Za is present at the para-position on $Ar_2$.

Another sub-structure which describes photoinitiators of Formula (I), has the general formula (Ib):

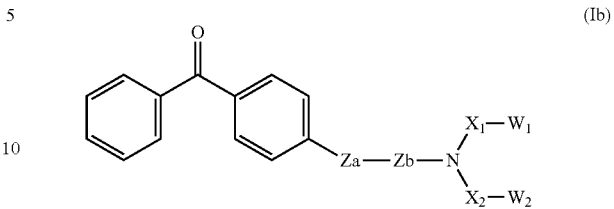

(Ib)

in which Za, Zb, N, $X_1$, $X_2$, $W_1$ and $W_2$, and preferred options for these groups, are as defined above.

Another sub-structure which describes photoinitiators of Formula (I) has the general formula (Ic):

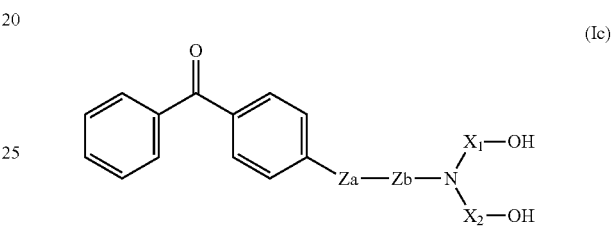

(Ic)

wherein Za, Zb, N, $X_1$, and $X_2$, and preferred options for these groups, are as defined above.

Suitable photoinitiators according to the invention include
{4-[bis(2-hydroxyethyl)amino]phenyl}(phenyl)methanone
[4-({2-[bis(2-hydroxyethyl)amino]ethyl}sulfanyl)phenyl] (phenyl)methanone
(4-{3-[bis(2-hydroxyethyl)amino]propoxy}phenyl)(phenyl) methanone
{4-[bis(2-hydroxypropyl)amino]phenyl}(phenyl)methanone
4-{3-[bis(2-hydroxyethyl)amino]propoxy}-1-chloro-9H-thioxanthen-9-one
4-[{2-[bis(2-hydroxyethyl)amino]ethyl}(methyl)amino]-1-chloro-9H-thioxanthen-9-one
2-[bis(2-hydroxyethyl)amino]ethyl[(9-oxo-9H-thioxanthen-2-yl)oxy]acetate
1-[bis(2-hydroxyethyl)amino]-4-propoxy-9H-thioxanthen-9-one
2-[(1-chloro-9-oxo-9H-thioxanthen-4-yl)oxy]-N,N-bis(2-hydroxyethyl)acetamide
1-{4-[bis(2-hydroxyethyl)amino]phenyl}-2-hydroxy-2-methylpropan-1-one
1-(4-{2-[bis(2-hydroxyethyl)amino]ethoxy}phenyl)-2-hydroxy-2-methylpropan-1-one
(3',5'-diisocyanatobiphenyl-4-yl)(phenyl)methanone.

Photoinitiators according to the invention of particular interest are
{4-[bis(2-hydroxyethyl)amino]phenyl}(phenyl)methanone
(4-{3-[bis(2-hydroxyethyl)amino]propoxy}phenyl)(phenyl) methanone
{4-[bis(2-hydroxypropyl)amino]phenyl}(phenyl)methanone
4-{3-[bis(2-hydroxyethyl)amino]propoxy}-1-chloro-9H-thioxanthen-9-one
2-[bis(2-hydroxyethyl)amino]ethyl[(9-oxo-9H-thioxanthen-2-yl)oxy]acetate
2-[(1-chloro-9-oxo-9H-thioxanthen-4-yl)oxy]-N,N-bis(2-hydroxyethyl)acetamide 1-(4-{2-[bis(2-hydroxyethyl)amino]ethoxy}phenyl)-2-hydroxy-2-methylpropan-1-one.

Polyurethane Polymers

The photoinitiators of the present invention may be used to promote polymerization in polyurethane polymers. To carry this out, the photoinitiators are mixed with suitable other monomers for PU formation, optionally with catalyst, and irradiated with UV radiation.

A general scheme for the formation of polyurethanes of Formula (III) using photoinitiators of Formula (I) is shown below:

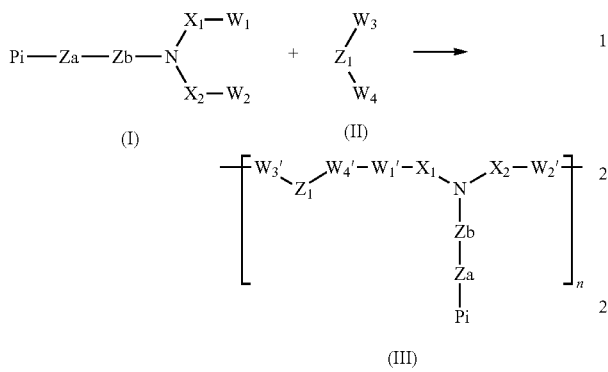

The photoinitiator of Formula I is as described above.

$Z_1$ is a linker moiety, independently selected from the same linker moieties defined above for Zb.

End groups $W_3$ and $W_4$ are independently selected from the same end groups as $W_1$ and $W_2$. $W_3$ and $W_4$ are selected so as to be complementary to $W_1$ and $W_2$, so that urethane and urethane-like chains are formed. For instance, if the end groups $W_1$, $W_2$ comprise alcohol, amine or thiol groups, suitable $W_3$ and $W_4$ will comprise isocyanate or isothiocyanate groups, and vice-versa.

Additional monomers may be introduced into the polyurethane according to the above scheme, as desired by the person skilled in the art. The additional monomers may be other photoinitiators of Formula I or other monomers of Formula II.

The weight of the photoinitiator (I) used to prepare polyurethane polymer (III) may be between 0.1% and 99% of the total mass of other monomers, suitably between 0.2% and 10%, most suitably 0.5% to 5%.

Suitably, the polyurethane polymer (III) has a molecular weight of more than 1 kDa, suitably between 10 kDa and 1000 kDa, most suitably between 20 kDa and 100 kDa.

As set out above, the photoinitiators of the present invention are incorporated into the polyurethane chain, as the end groups $W_1$, $W_2$ react with the end groups $W_3$, $W_4$ of other monomers. The nomenclature $W_1'$, $W_2'$, $W_3'$ and $W_4'$ depict the corresponding end groups $W_1$-$W_4$ after being reacted.

The photoinitiator moiety therefore becomes pendant from the polyurethane backbone. As such, it is not able to leach from the polyurethane matrix. In addition, radical bond-forming reactions between the photoinitiator moiety and other components of the polymerization mixture will cause cross-linking, rather than forming undesirable low molecular weight compounds.

It has been found that the photoinitiators of the present invention act to cure polyurethane polymers, at least as effectively, if not more effectively than known photoinitiators.

In addition, polyurethane films comprising the photoinitiators of the present invention exhibit good adhesion in film form to hydrophobic surfaces, such as polypropylene.

The following synthesis schemes show synthetic routes to photoinitiators of structure Ib.

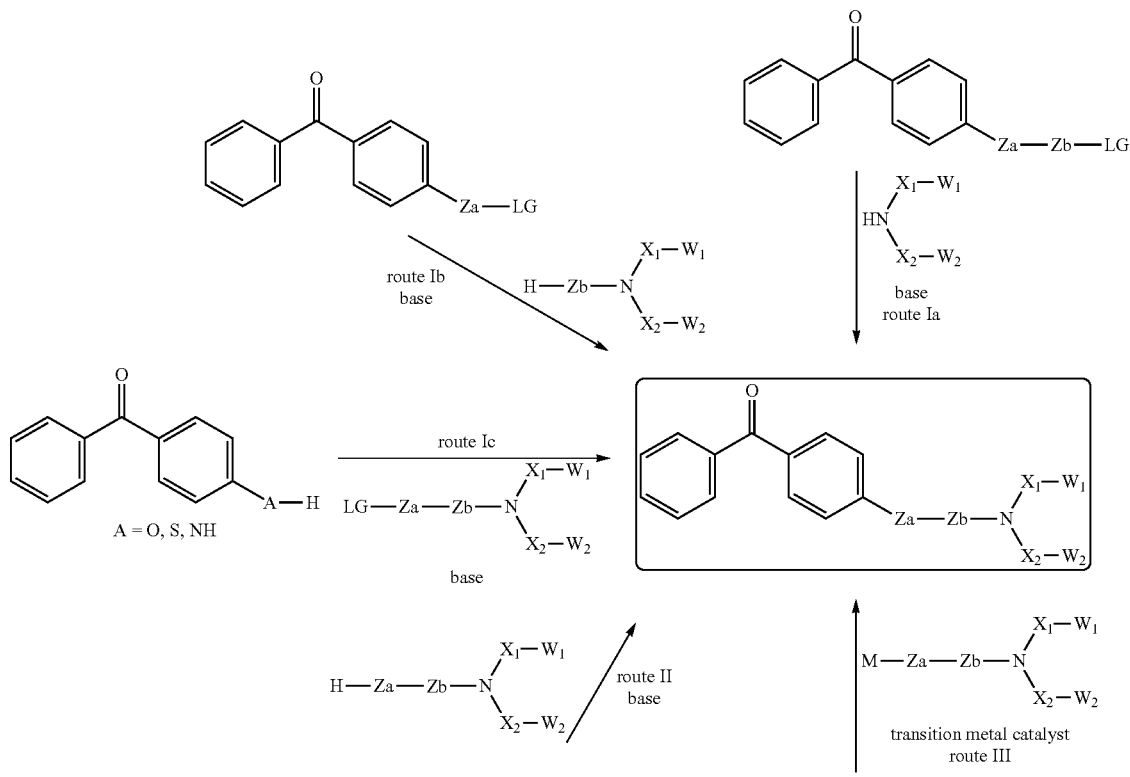

-continued

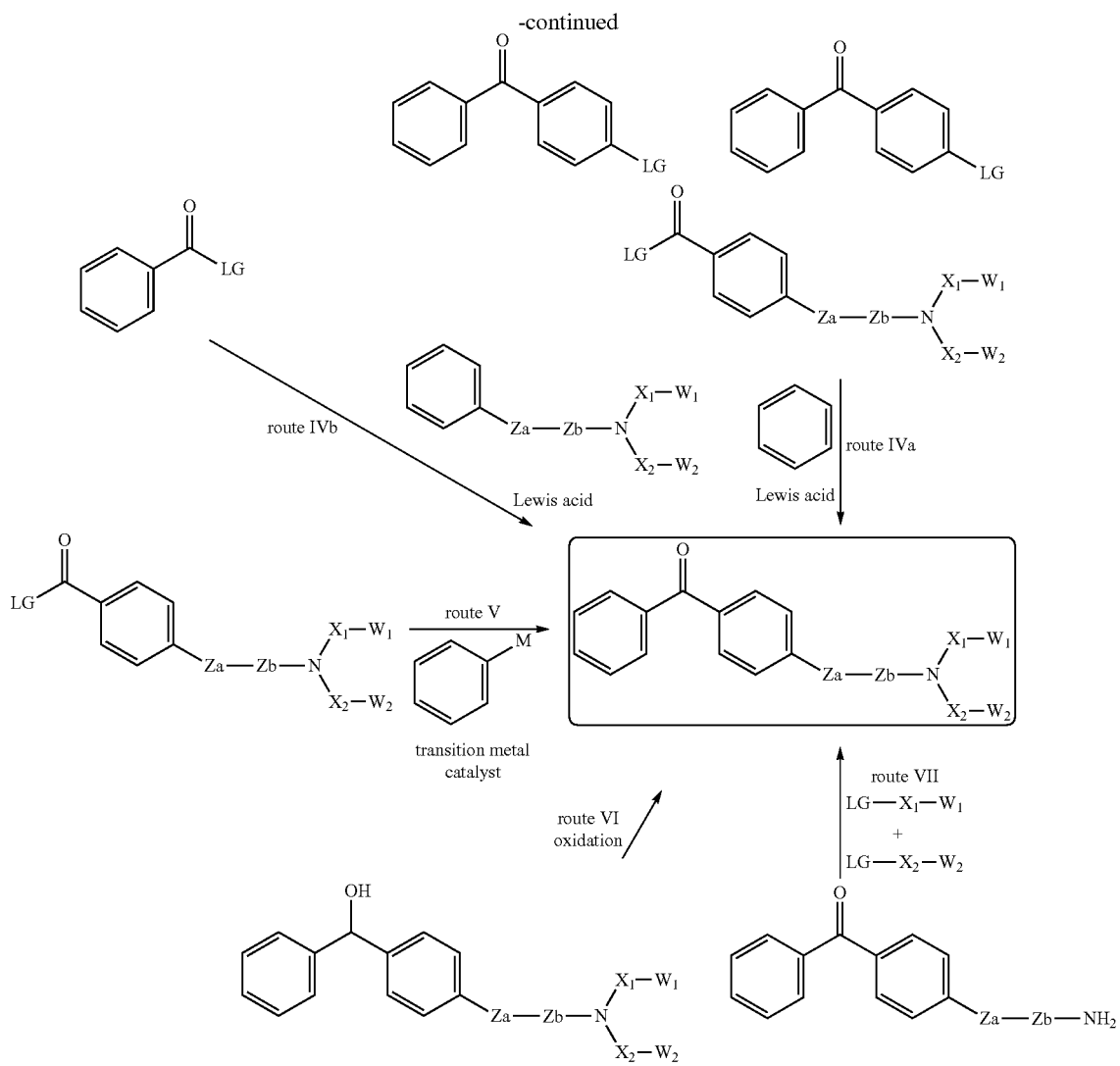

Routes Ia, Ib and Ic are nucleophilic substitution, or carbonyl group transformation (i.e. nitrogen acylation). LG depicts a leaving group (preferably Cl, Br, I, OMs, OTs, OTf). The base used is preferably amine, alkali metal alkoxide, hydroxide or carbonate.

Route II is a nucleophilic aromatic substitution. LG depicts a leaving group (preferably F, Cl). The base is preferably amine, alkali metal alkoxide, hydroxide or carbonate.

Route III is a cross-coupling reaction. LG depicts a leaving group (preferably Cl, Br, I, OMs, OTs, OTf). M depicts a nucleophilic organometallic substituent (preferably $R_2Al—$, $RZn—$, $R_3Sn—$, $RMg—$, $Li—$, $(RO)_2B—$). The transition metal catalyst is a salt or transition metal complex (preferably containing Pd, Pt, Ni, Ir, Rh, Ru, Cu, Fe).

Routes IVa and IVb are Friedel-Crafts acylations. The Lewis acid may be preferably $BF_3$, $BCl_3$, $AlCl_3$, $FeCl_3$ or $SnCl_4$.

Route V may be a reaction of an aryl organometallic reagent with an acyl derivative. M depicts a nucleophilic organometallic substituent (preferably $RMg—$, $RZn—$, $RCd—$ or $R_3Sn—$). Route VI is oxidation of a diarylmethanol. Preferable oxidants include manganese, ruthenium, chromium reagents and Swern oxidation.

Route VII may be nitrogen alkylation or acylation. Suitably, one or both reagents $LG-X_1—W_1$ and $LG-X_2—W_2$ may contain an epoxide (aziridine) which is opened by the nucleophilic nitrogen to reveal a reactive hydroxy (amino) end group.

The invention therefore provides a method for the synthesis of a photoinitiator, said method comprising the steps of:
  a. reacting a photoinitiator moiety Pi having at least one —OH, —SH or —NHR$^1$ substituent, wherein R$^1$ is H or optionally substituted $C_1$-$C_{12}$ alkyl, in a nucleophilic substitution reaction with a substance having the formula X—($C_1$-$C_{12}$ alkylene)-Y; in which X is a leaving group which can be displaced by said —OH, —SH or —NHR$^1$ substituent, and Y is a leaving group which cannot be displaced by said —OH, —SH or —NHR$^1$ substituent;
  b. reacting the product of step a. with sodium iodide so as to replace leaving group Y with an iodide; and
  c. reacting the product of step ii. with an amine of the formula:

in which $W_1$, $W_2$, $X_1$ and $X_2$ are as defined herein.

Suitable leaving groups X are Cl, Br, I, OMs, OTs and OTf. Suitable leaving groups Y are Cl, Br, OMs, OTs and OTf. Further details of the method are evident from the following examples.

EXAMPLE 1

4-{3-[bis(2-hydroxyethyl)amino]propoxy}benzophenone

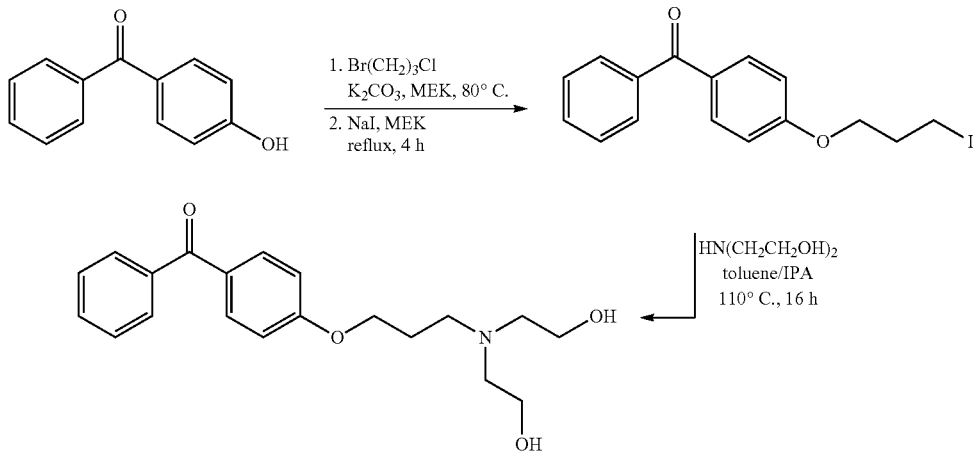 [SMILES: O=C(c1ccccc1)c1ccc(O)cc1 ; O=C(c1ccccc1)c1ccc(OCCCI)cc1 ; O=C(c1ccccc1)c1ccc(OCCCN(CCO)CCO)cc1]

RELEVANT LITERATURE: J. Med. Chem. 2001, 3810-3820; J. Med. Chem. 1998, 3976-3986; J. Med. Chem. 1989, 105-118.

Small Scale:

A 1000 mL three-neck flask was charged with 4-hydroxybenzophenone (50.00 g; 252.2 mmol), 1-bromo-3-chloropropane (79.41 g; 504.4 mmol) and 2-butanone (500 mL). After flushing with nitrogen, anhydrous potassium carbonate (104.6 g; 756.5 mmol) was added and the reaction mixture was stirred at reflux for 24 h. Full consumption of the starting 4-hydroxybenzophenone was confirmed by TLC. The reaction mixture was filtered, the filtrate evaporated, the oily residue dissolved in dichloromethane (300 mL) and extracted with water (3×100 mL). The organic phase was separated, evaporated, and the unreacted 1-bromo-3-chloropropane was removed by heating to 70° C. in vacuo. The residue was dissolved in 2-butanone (500 mL) and sodium iodide (45.36 g; 302.6 mmol) was added. The reaction mixture was refluxed for 6 h. The reaction mixture was filtered, the filtrate evaporated, the oily residue dissolved in dichloromethane (300 mL) and extracted with water (3×100 mL). The organic phase was separated, evaporated, the light brown oily residue dried in vacuo to give crude 4-(3-iodopropoxyl)benzophenone (light brown solid; 83.2 g).

To the crude product from the previous step (83.2 g; 227.2 mmol) was added toluene (100 mL), 2-propanol (200 mL) and diethanolamine (179.2 g; 1.704 mol). The reaction mixture was refluxed (110° C.) for 16 h. After evaporation of ethanol and toluene, water (2000 mL) was added to precipitate the oily product. The emulsion obtained was thoroughly extracted with diethyl ether (6×300 mL). The aqueous phase was discarded and the organic phase was extracted with hydrochloric acid (6M, 3×200 mL). The pH of the strongly acidic aqueous phase was adjusted to 12-13 by slow addition of 35% aq. ammonia to reprecipitate the product. The aqueous phase was reextracted with dichloromethane (3×300 mL), the organic phase dried (MgSO$_4$), evaporated and the light brown oily product dried in vacuo.

This provides 4-{3-[bis(2-hydroxyethyl)amino]propoxy}benzophenone (57.7 g; 74% yield).

1H-NMR (400 MHz, chloroform-d): 7.80 (d, J=8.8 Hz, 2H), 7.73 (d, J=8.3 Hz, 2H), 7.55 (m, 1H), 7.46 (t, J=7.8 Hz, 2H), 6.95 (d, J=8.8 Hz, 2H), 4.12 (t, J=6.0 Hz, 2H), 3.62 (t, J=5.3 Hz, 4H), 2.87 (bs, 2H), 2.75 (t, J=6.9 Hz, 2H), 2.67 (t, J=5.3 Hz, 4H), 1.96 (apparent quintet, J=6.4 Hz, 2H). UV (MeCN): $\lambda_{max}$=286 nm.

Large Scale:

A 5000 mL three-neck flask was charged with 4-hydroxybenzophenone (800.0 g; 4.036 mol), 1-bromo-3-chloropropane (832.5 g; 5.288 mol) and 2-butanone (3300 mL). Anhydrous potassium carbonate (673.6 g; 4.874 mol) was added and the reaction mixture was stirred at reflux for 100 h. Full consumption of the starting 4-hydroxybenzophenone was confirmed by HPLC. The reaction mixture was filtered, the inorganic solids were washed with 2-butanone (3×100 mL). The filtrate was evaporated, and the unreacted 1-bromo-3-chloropropane was removed by heating to 70° C. in vacuo. The residue was dissolved in acetonitrile (2000 mL) and sodium iodide (650.0 g; 4.337 mol) was added. The reaction mixture was refluxed for 8 h. The reaction mixture was filtered to give a solution of crude 4-(3-iodopropoxyl)benzophenone.

The crude acetonitrile solution from the previous stage was charged over a period of 6 hours into neat diethanolamine (2800 g; 26.63 mol) heated to 70° C. After the end of the feed, the reaction mixture heated to reflux for a further 2 h. Full consumption of the starting material was confirmed by TLC. The reaction mixture was poured into water (10 L) and the resulting suspension extracted with dichloromethane (3×1500 mL). The organic phase was separated and extracted with 1 M aq. HCl (4000 mL). The organic phase was discarded and the aqueous phase was made strongly alkaline (pH 12) by slow addition of 50% aq. NaOH. The resulting suspension was extracted with dichloromethane (3×1000 mL). The organic layer was dried (MgSO$_4$), filtered and evaporated. The light brown oil was dried in high vacuo at 80° C. This provides 4-{3-[bis(2-hydroxyethyl)amino]propoxy}benzophenone (1180 g; 85.1% yield over 3 steps).

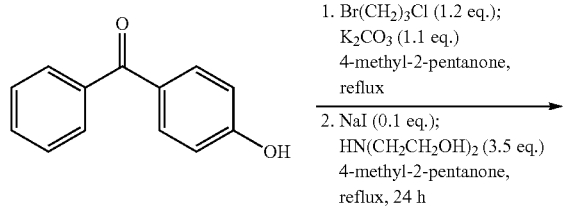

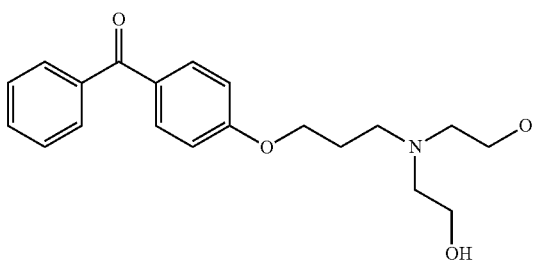

EXAMPLE 2

4-{3-[bis(2-hydroxyethyl)amino]propoxy}-1-chloro-9H-thioxanthen-9-one

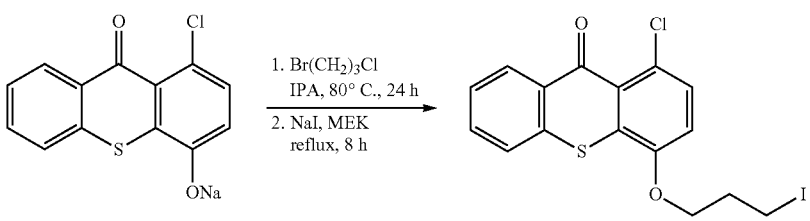

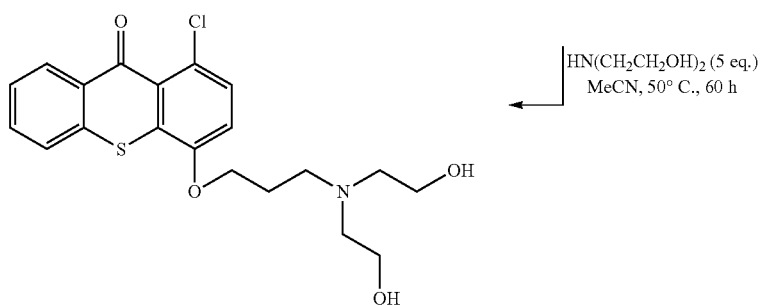

Alternative Procedure:

A 500 mL three-neck flask was charged with 4-hydroxybenzophenone (80.00 g; 0.4036 mol), 1-bromo-3-chloropropane (76.25 g; 0.4843 mol) and 4-methyl-2-pentanone (330 mL). Anhydrous potassium carbonate (61.36 g; 0.4440 mol) was added and the reaction mixture was stirred at reflux (120° C.) for 4 h. HPLC analysis shows that the reaction mixture contains 90.0% 4-(3-chloropropoxyl)benzophenone; 7.0% 1,3-bis(4-benzoylphenoxy)propane and 0.8% 4-hydroxybenzophenone. The reaction mixture was filtered hot and the inorganic solids were washed with 4-methyl-2-pentanone (100 mL). The filtrate was charged into a mixture of diethanolamine (148.5 g; 1.412 mol), sodium iodide (6.05 g; 0.0404 mol) and 4-methyl-2-pentanone (150 mL). The reaction mixture heated to reflux (122° C.) for 24 h. The reaction mixture was cooled to room temperature and extracted with water (500 mL). The organic phase was extracted with 1 M HCl (500 mL) at 70° C. to prevent crystallisation of the 1,3-bis(4-benzoylphenoxy)propane byproduct. The aqueous phase was separated, cooled to room temperature and taken to pH 12 with 50% aqueous NaOH. The resulting emulsion was extracted with 4-methyl-2-pentanone (3×200 mL). The organic phase was separated, dried (MgSO$_4$), filtered and the solvent removed in vacuo. This provides 4-{3-[bis(2-hydroxyethyl)amino]propoxy}benzophenone (123.2 g; 89% yield over 3 steps).

Small Scale:

A 500 mL flask was charged with the sodium salt of 1-chloro-4-hydroxy-9H-thioxanthen-9-one (28.5 g; 0.100 mol), 1-bromo-3-chloropropane (17.4 g; 0.111 mol) and isopropyl alcohol (280 mL). The turbid reaction mixture was refluxed for 24 h. The hot solution was diluted with isopropyl alcohol (130 mL), drowned out in water (1400 mL) and the resulting suspension was extracted with dichloromethane (3×250 mL). The organic phase was separated, dried (MgSO$_4$), filtered and solvent removed in vacuo to give 1-chloro-4-(3-chloropropoxy)-9H-thioxanthen-9-one (24.4 g; 72% yield).

1-H NMR (400 MHz, CDCl$_3$): 8.39 (ddd, J=8.1, 1.5, 0.6 Hz, 1H), 7.54 (m, 1H), 7.48 (ddd, J=8.1, 1.4, 0.6 Hz), 7.41 (m, 1H), 7.33 (d, J=8.6 Hz, 1H), 6.92 (d, J=8.6 Hz, 1H), 4.23 (t, J=5.8 Hz, 2H), 3.83 (t, J=6.3 Hz, 2H), 2.32 (apparent quintet, J=6.0 Hz, 2H).

The crude product from the previous step (26.44 g; 77.94 mmol) was suspended in 2-butanone (250 mL) and sodium iodide (14.02 g; 93.52 mmol) was added. The reaction mixture was refluxed for 16 h. The reaction mixture was filtered, the solids were washed with boiling 2-butanone (2×50 mL), the filtrate evaporated, the oily residue dissolved in dichloromethane (300 mL) and extracted with water (2×100 mL). The organic phase was separated, evaporated and dried in vacuo to give crude 1-chloro-4-(3-iodopropoxy)-9H-thioxanthen-9-one (30.51 g; yellow solid; 91% yield).

1-H NMR (400 MHz, CDCl$_3$): 8.53 (dd, J=9.0, 1.4 Hz, 1H), 7.59 (m, 1H), 7.53 (dd, J=8.9, 1.5 Hz, 1H), 7.45 (m, 1H), 7.37 (d, J=9.6 Hz, 1H), 6.91 (d, J=9.6 Hz, 1H), 3.83 (t, J=6.3 Hz, 2H), 3.03 (t, J=7.4 Hz, 2H), 1.81 (apparent quintet, J=6.9 Hz, 2H).

Crude 1-chloro-4-(3-iodopropoxy)-9H-thioxanthen-9-one (10.0 g; 23.22 mmol) from the previous step was slowly charged into a solution of diethanolamine (14.65 g; 139.3 mmol) in acetonitrile (100 mL) heated to 50° C. The reaction mixture was stirred vigorously and heated to 50° C. for 60 h. The solvent was removed in vacuo and water (500 mL) was added. The mixture was extracted with dichloromethane (3×250 mL). The aqueous phase was discarded and the organic phase was extracted with hydrochloric acid (2M, 3×100 mL). The pH of the strongly acidic aqueous phase was adjusted to 12-13 by slow addition of 50% aq. NaOH to reprecipitate the product. The aqueous phase was reextracted with dichloromethane (4×100 mL), the organic phase dried (MgSO$_4$), evaporated to give 4-{3-[bis(2-hydroxyethyl)amino]propoxy}-1-chloro-9H-thioxanthen-9-one (5.31 g; 56% yield).

$^1$H-NMR (400 MHz, CDCl$_3$): 8.29 (ddd, J=8.1, 1.5, 0.6 Hz, 1H), 7.45 (ddd, J=8.2, 6.8, 1.4 Hz, 1H), 7.39 (ddd, J=8.1, 1.4, 0.6 Hz, 1H), 7.34 (ddd, J=8.2, 6.8, 1.4 Hz, 1H), 7.21 (d, J=8.6 Hz, 1H), 6.81 (d, J=8.6 Hz, 1H), 4.04 (t, J=6.1 Hz, 2H), 3.64 (bs, 2H), 3.59 (t, J=5.2 Hz, 4H), 2.73 (t, J=6.8 Hz, 2H), 2.63 (t, J=5.2 Hz, 4H), 1.94 (apparent quintet, J=6.4 Hz, 2H).

Large Scale Prep:

A 1000 mL three-neck flask was charged with 1-chloro-4-hydroxy-9H-thioxanthen-9-one (100.0 g; 0.381 mol), 1-bromo-3-chloropropane (71.9 g; 0.457 mol), anhydrous potassium carbonate (63.1 g; 0.457 mol) and 2-butanone (500 mL). The mixture was stirred at reflux for 60 h. Full conversion was confirmed by TLC. The reaction mixture was filtered through a glass sinter, the inorganic solids were washed with warm dichloromethane (4×100 mL). The filtrate was evaporated to dryness to give a bright yellow solid. The crude 1-chloro-4-(3-chloropropoxy)-9H-thioxanthen-9-one (129.1 g) was dissolved in 2-butanone (400 mL) and sodium iodide (62.8 g; 0.419 mol) was added. The reaction mixture was refluxed for 16 h, filtered hot, the solids were washed with boiling 2-butanone (2×100 mL) and the filtrate evaporated to dryness.

The crude product from the previous step was suspended in THF (300 mL) and the suspension was charged over 30 min to neat diethanolamine (240.1 g; 2.28 mol) at 60° C. The reaction was heated to reflux for 3 h. The clear yellow-brown solution was poured into water (2000 mL) and extracted with ethyl acetate (3×750 mL). The aqueous phase was discarded and the organic phase was extracted with hydrochloric acid (1M, 3×500 mL). The pH of the strongly acidic aqueous phase was adjusted to 12-13 by slow addition of 50% aq. NaOH to reprecipitate the product. The aqueous phase was reextracted with dichloromethane (4×500 mL), the organic phase dried (MgSO$_4$) and evaporated to dryness to give 4-{3-[bis(2-hydroxyethyl)amino]propoxy}-1-chloro-9H-thioxanthen-9-one (99.8 g; 64% yield).

EXAMPLE 3

{4-[bis(2-hydroxyethyl)amino]phenyl}-(phenyl)methanone

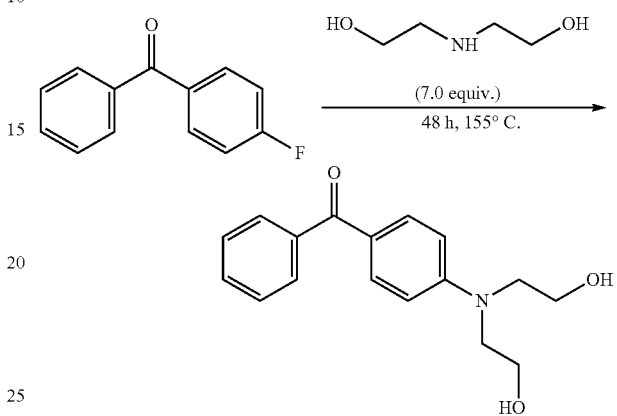

RELEVANT LITERATURE: *J. Phys. Org. Chem.* 2001, 14, 247-255; *J. Med. Chem.* 1991, 34, 1552-1560.

A 100 mL two-neck flask was charged with 4-fluorobenzophenone (15.0 g; 74.9 mmol) and diethanolamine (55.1 g; 524 mmol). The flask was flushed with nitrogen, fitted with a reflux condenser and heated to 155° C. for 48 h under a gentle stream of nitrogen. Complete conversion of the starting 4-fluorobenzophenone was confirmed by TLC. After cooling to ambient temperature, the dark viscous reaction mixture was poured into water (2000 mL). The resulting suspension was thoroughly extracted with diethyl ether (6×250 mL). The aqueous phase was discarded and the organic phase was extracted with hydrochloric acid (2M, 5×200 mL). The pH of the strongly acidic aqueous phase was adjusted to 12-13 by slow addition of 35% aq. ammonia to reprecipitate the product. The aqueous phase was then reextracted with dichloromethane (3×300 mL). The crude organic extract was purified by passing through a short silica gel column (eluent: ethyl acetate). The eluted yellow solution was evaporated and the oily residue dried in vacuo to provide {4-[bis(2-hydroxyethyl)amino]phenyl}(phenyl)methanone (yellow-brown solid; 13.176 g; 62% yield).

$^1$H-NMR (400 MHz, CDCl$_3$): 7.72 (d, J=10.0 Hz, 2H), 7.69-7.66 (m, 2H), 7.53 (tt, J=8.2, 1.4 Hz, 1H), 7.42 (t, J=8.3 Hz, 2H), 6.55 (d, J=10.0 Hz, 2H), 4.22 (bs, 2H), 3.43 (t, J=5.4 Hz, 4H), 3.20 (t, J=5.4 Hz, 4H).

$^{13}$C-NMR (100 MHz, CDCl$_3$): 195.5, 151.5, 138.7, 132.8, 131.4, 129.4, 128.0, 124.8, 111.0, 60.1, 54.9.

EXAMPLE 4

General Procedure the for Preparation of Polyurethanes in Solvent

A glass vial was charged with a reactive photoinitiator and a reactive polyether (amounts given in Table 1). The reaction vessel was heated to 120-130° C. under vacuum for 1 h to remove all moisture. The reaction vessel was then allowed to cool under vacuum, fitted with a reflux condenser and flushed with nitrogen. Dry chlorobenzene was added and the reaction was stirred at 60° C. to obtain a homogeneous clear solution with 30 wt % of solids. Appropriate amount of diisocyanate was added via syringe and the reaction mixture was heated under reflux for 16 h. The viscous yellow mixture was evaporated in vacuo, residual chlorobenzene was removed by co-evaporation with MeOH-water. The resulting gummy solid was dried in vacuo for 4-6 h at 75° C. This provided the appropriate polyurethane polymer as a light yellow-brown gummy solid.

EXAMPLE 5

Solvent-Free Procedure the for Preparation of Polyurethanes

A glass vial was charged with a reactive photoinitiator and a reactive polyether (amounts given in Table 2). The reaction vessel was heated to 120-130° C. under vacuum for 1 h to remove all moisture. The flask was allowed to cool to 70° C. and charged with the appropriate amount of diisocyanate (given in Table 2). The reaction melt was then heated with stirring to 70° C. for 16 h. This provided the appropriate photochromic polymer as a white to light yellow solid.

Figure 2:
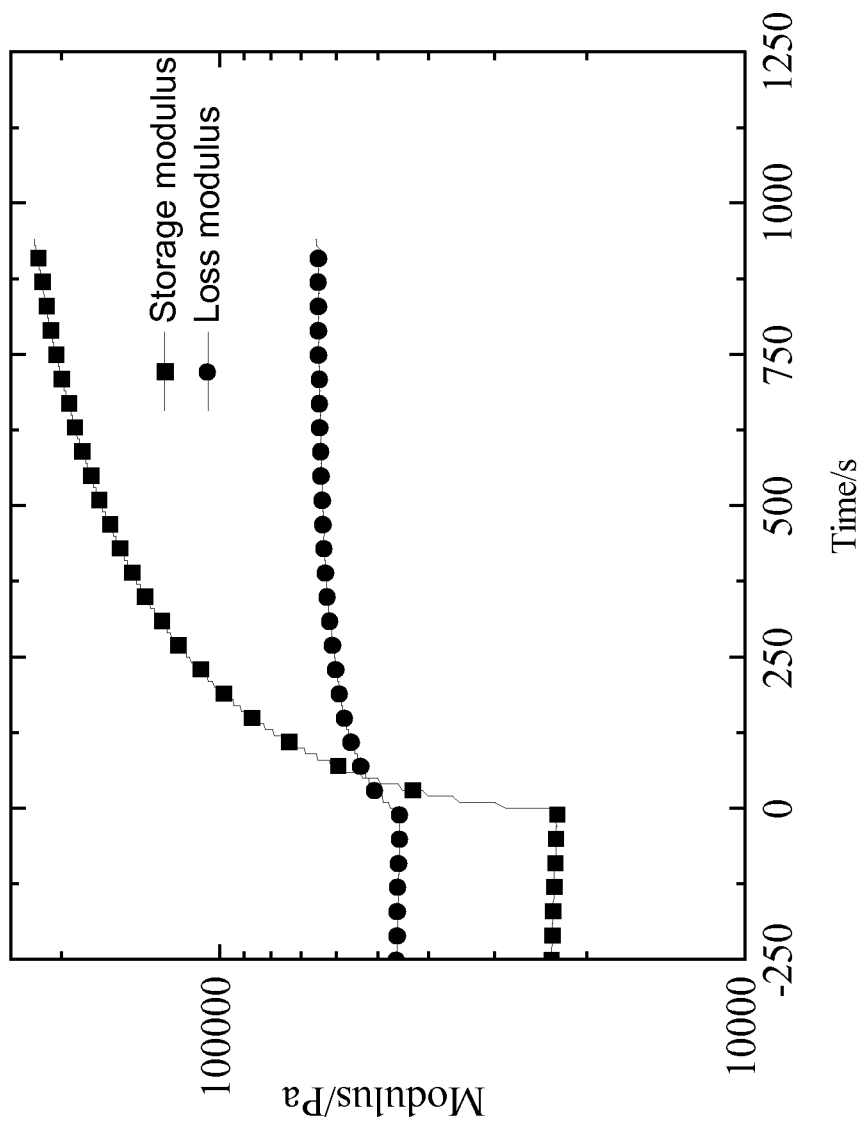
FIG. 2 shows the changes of rheological properties of a pristine sample of a PU made from 4-{3-[bis(2-hydroxyethyl)amino]propoxy}benzophenone (0.5 wt %), Tecophilic (99.2 wt %) and Irganox 1010 (0.5 wt %) subjected to UV light.

Tecophilic (99.2 wt %) and Irganox 1010 (0.5 wt %))). The polymer was processed to a plate using a heat press. A disc was cut from this plate (Ø25 mm) and placed in a plate-plate rheometer, where the bottom plate consists of a quartz window. Rheological properties were measured at 1 Hz at 120° C. (see FIG. 2), where a UV-light source irradiating the polyurethane sample through the quartz plate was turned on at t=0 s. After approximately 60 s the sample passes a transition from a liquid state to a solid state, i.e. a gel-point, which demonstrates that the photoinitiator moieties within the polyurethane are actually responsible for curing the sample when exposed to UV light.

Although the invention has been described with reference to a number of examples and reaction schemes, it should not be considered as limited by the above description. The full scope of the invention is defined by the appended claims.

TABLE 1

Composition and GPC characterisation of photochromic polyurethanes prepared in solvent

| reactive PI | wt % | reactive polyether | wt % | diisocyanate | wt % | polymer Mw | Mw/Mn |
|---|---|---|---|---|---|---|---|
| 4-{3-[bis(2-hydroxyethyl)amino]propoxy}benzophenone | 2 | PEG-2000 | 85 | HMDI | 13 | 76 kDa | 1.92 |
| 4-{3-[bis(2-hydroxyethyl)amino]propoxy}benzophenone | 10 | PEG-2000 | 73 | HMDI | 17 | 78 kDa | 2.27 |
| 4-{3-[bis(2-hydroxyethyl)amino]propoxy}benzophenone | 2 | Jeffamine D-4000 | 91 | HMDI | 7 | 35 kDa | 2.19 |
| 4-{3-[bis(2-hydroxyethyl)amino]propoxy}-1-chloro-9H-thioxanthen-9-one | 2 | PEG-2000 | 85 | HMDI | 13 | 43 kDa | 1.76 |
| 4-{3-[bis(2-hydroxyethyl)amino]propoxy}-1-chloro-9H-thioxanthen-9-one | 10 | PEG-2000 | 74 | HMDI | 16 | 29 kDa | 1.62 |
| 4-{3-[bis(2-hydroxyethyl)amino]propoxy}-1-chloro-9H-thioxanthen-9-one | 2 | Jeffamine D-4000 | 91 | HMDI | 7 | 32 kDa | 2.06 |

TABLE 2

Composition and GPC characterisation of photochromic polyurethanes prepared under solvent-free conditions

| reactive PI | wt % | reactive polyether | wt % | diisocyanate | wt % | polymer Mw |
|---|---|---|---|---|---|---|
| 4-{3-[bis(2-hydroxyethyl)amino]propoxy}benzophenone | 2 | PPG-2000 | 89 | HDI | 9 | 50 kDa |
| 4-{3-[bis(2-hydroxyethyl)amino]propoxy}benzophenone | 2 | PPG-4000 | 93 | HDI | 5 | 45 kDa |
| 4-{3-[bis(2-hydroxyethyl)amino]propoxy}benzophenone | 2 | PPG-2000 | 85 | HMDI | 13 | 24 kDa |
| 4-{3-[bis(2-hydroxyethyl)amino]propoxy}benzophenone | 2 | PPG-4000 | 91 | HMDI | 7 | 21 kDa |
| 4-{3-[bis(2-hydroxyethyl)amino]propoxy}benzophenone | 2 | PEG-2000 | 89 | HDI | 9 | 53 kDa |
| 4-{3-[bis(2-hydroxyethyl)amino]propoxy}benzophenone | 2 | PEG-4600 | 94 | HDI | 4 | 62 kDa |

EXAMPLE 6

UV Curing of Polyurethanes

A polyurethane was prepared from example 1 (4-{3-[bis(2-hydroxyethyl)amino]propoxy}benzophenone (0.5 wt %),

The invention claimed is:

1. A photoinitiator of the formula (I):

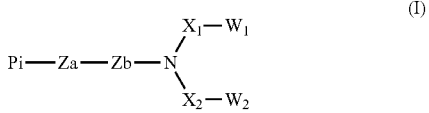

in which:

Pi is a phenyl hydroxyalkyl ketone photoinitiator moiety;

Za and Zb together form a single bond, or a linker in which
Za is selected from optionally substituted —O—($C_1$-$C_{12}$ alkylene))$_n$-, optionally substituted —(N$R^1$—($C_1$-$C_{12}$ alkylene))$_n$ wherein $R^1$ is H or optionally substituted $C_1$-$C_{12}$ alkyl and optionally substituted —(S—($C_1$-$C_{12}$ alkylene))$_n$-; wherein n is 1; wherein Za is joined to Pi via the O, N or S atom in Za; and Zb is a single bond;

$X_1$ and $X_2$ are independently selected from optionally substituted $C_1$-$C_{12}$ alkylene, optionally substituted $C_1$-$C_{12}$ alkenylene, optionally substituted heterocyclyl, —O—, —S—, —N$R^2$—, —C(=O)—, —C(=N$R^2$)—, —Si($R^2$)$_2$—O—, optionally substituted aryl, and combinations thereof, wherein $R^2$ is H or optionally substituted $C_1$-$C_{12}$ alkyl;

wherein $X_1$ and $X_2$ may be linked to one another or to Za to form one or more ring structures;

wherein Za, $X_1$ and $X_2$ are selected such that N is a tertiary amine;

$W_1$ and $W_2$ are independently selected from the group consisting of —OH, —N$H_2$, —NH$R_3$ and —SH, wherein $R_3$ is an optionally substituted $C_1$-$C_{12}$ alkyl.

2. A photoinitiator according to claim 1, wherein $W_1$ and $W_2$ are the same.

3. A photoinitiator according to claim 1, wherein $X_1$ and $X_2$ are independently selected from optionally substituted $C_1$-$C_{12}$ alkylene, —O—, —S—, —N$R^2$—, wherein $R^2$ is H or optionally substituted $C_1$-$C_{12}$ alkyl, and combinations thereof.

4. A photoinitiator according to claim 1, wherein $X_1$ and $X_2$ may be linked to one another to form one or more ring structures.

5. A photoinitiator according to claim 1, wherein $X_1$ and $X_2$ are independently selected from optionally substituted $C_1$-$C_{12}$ alkylene, preferably optionally substituted $C_1$-$C_6$ alkylene.

6. A photoinitiator according to claim 1, wherein $X_1$ and $X_2$ are the same.

7. A photoinitiator according to claim 1, wherein Za is selected from optionally substituted —O—($C_1$-$C_{12}$ alkylene)-, preferably optionally substituted —O—($C_1$-$C_6$ alkylene)-.

8. A photoinitiator according to claim 1, wherein $X_1$ and $X_2$ are independently selected from optionally substituted $C_1$-$C_{12}$ alkylene, and $W_1$ and $W_2$ are —OH.

9. A photoinitiator according to claim 1, selected from the group consisting of
   1-{4-[bis(2-hydroxyethyl)amino]phenyl}-2-hydroxy-2-methylpropan-1-one, and
   1-(4-{2-[bis(2-hydroxyethyl)amino]ethoxy}phenyl)-2-hydroxy-2-methylpropan-1-one.

10. A photoinitiator according to claim 1, being
    1-(4-{2-[bis(2-hydroxyethyl)amino]ethoxy}phenyl)-2-hydroxy-2-methylpropan-1-one.

* * * * *